United States Patent [19]
Bryant et al.

[11] Patent Number: 5,545,635
[45] Date of Patent: Aug. 13, 1996

[54] INHIBITING BONE LOSS WITH EQUILENIN

[75] Inventors: Henry U. Bryant; Jeffrey A. Dodge, both of Indianapolis; Masahiko Sato, Carmel; Na N. Yang, Indianapolis, all of Ind.

[73] Assignee: Eli Lilly and Company, Indianapolis, Ind.

[21] Appl. No.: 448,061

[22] Filed: May 23, 1995

[51] Int. Cl.⁶ ..................................................... A61K 31/56
[52] U.S. Cl. ........................................... 514/177; 514/178
[58] Field of Search ....................................... 514/178, 177

[56] References Cited

U.S. PATENT DOCUMENTS 4,154,820  5/1979  Simoons .................................. 424/175

OTHER PUBLICATIONS

Prestwood, K. M., et al., *J. Clin. Endocrinol. Metab.*, 79(2):366–371 (1994).

Genant H. K., et al., *Obstet. Gynecol.*, 76(4):579–584 (1990).

Von Beck, A., et al., *Wein Klin Wochenschr*, 87(2):59–62 (1975).

Bhavnani, B. R., *Endocrine Reviews*, 9(4):396–416 (1988).

Washburn, S. A. et al., *Am. J. Obstet. Gynecol.*, 169:(2, I):251–256 (1993).

Wronski, T. J., et al., *Endocrinology*, 123(2):681–686, (1988).

*Primary Examiner*—Theodore J. Criares
*Attorney, Agent, or Firm*—James J. Sales; David E. Boone

[57] ABSTRACT

The present invention provides methods of inhibiting bone loss in humans comprising administering to a patient in need of treatment an effective amount of d-equilenin, 17β-dihydroequilenin, and 17α-dihydroequilenin, and pharmaceutical formulations thereof.

7 Claims, No Drawings

INHIBITING BONE LOSS WITH EQUILENIN

The present invention relates to the fields of pharmacology and pharmaceutical chemistry, and provides methods for inhibiting the loss of bone in humans.

The current major diseases or conditions of bone which would benefit from the present invention include post-menopausal osteoporosis, hysterectomy patients, senile osteoporosis, patients undergoing long-term treatment of corticosteroids, side effects from glucocorticoid or steroid treatment, patients suffering from Cushings's syndrome, gonadal dysgensis, periarticular erosions in rheumatoid arthritis, osteoarthritis, Paget's disease, osteohalisteresis, osteomalacia, hypercalcemia of malignancy, osteopenia due to bone metastases, periodontal disease, and hyperparathyroidism.

All of these conditions are characterized by net bone loss, resulting from an imbalance between the degradation of bone (bone resorption) and the formation of new healthy bone.

One of the most common bone disorders is post-menopausal osteoporosis which affects the majority of women over 60 years old in the United States. Women after menopause experience an increase in the rate of bone turnover with resulting net loss of bone, as circulating estrogen levels decrease. The rate of bone turnover differs between bones and is highest in sites enriched with trabecular bone, such as the vertebrae and the femoral head. The potential for bone loss at these sites immediately following menopause is 4–5% per year. The resulting decrease in bone mass and enlargement of bone spaces leads to increased fracture risk, as the mechanical integrity of bone deteriorates rapidly.

Approximately, 20–25 million women, and an increasing group of men, have detectable vertebral fractures, with an additional 250,000 hip fractures reported yearly in America alone. The latter case is associated with a 12% mortality rate within the first two years with about 30% of the patients requiring nursing home care after fracturing. Therefore, the consequences are an increase in morbidity, loss of stature, mobility and quality of life, and an increase in mortality due to complications from slow or imperfect healing of bone fractures. The economic consequences, while already significant, are expected to increase because of the aging population in industrialized nations.

Post-menopausal osteoporosis is characterized by the large and rapid loss of bone due to the cessation of estrogen production by the ovaries. Indeed, the current preferred treatment in the United States and many other countries is estrogen replacement therapy to limit the progression of osteoporotic bone loss. Although estrogens have beneficial effects on bone and cardiovascular tissues, patient compliance has been poor because of side effect problems, including the resumption of menses, mastodynia, an increase in the risk of uterine cancer, and a perceived increase in the risk of breast cancer. In addition, osteoporotic men are likely to object to estrogen treatment.

One "estrogen" which is frequently prescribed as the primary treatment in a hormone replacement therapy regime, is Premarin®. Premarin is a well recognized composition extracted from pregnant mare's urine, comprised of approximately 45% estrone sulfate, 25% equilin sulfate, 15% 17α-dihydroequilin sulfate, and trace amounts of other B-ring unsaturated and classical estrogens such as equilenin, 17α-dihydroequilin, 17β-estradiol, 17β-dihydroequilin, 17β-dihydroequilenin, 17α-esnradiol, and 17α-dihydroequilenin. Each of these trace components exist in Premarin as sulfate esters. Although the majority of Premarin's components exist in trace amounts, it is recognized in the art than the biological effects of Premarin, including its activity in inhibiting bone loss, are the sum of the effects of the various components [see, e g., Bhavnoni, B. R., *Endocrine Reviews*, 9(4): 396–416, 406 (1988)]. Conversely, the present invention relates to the discovery that certain components of Premarin or, more accurately, certain components of pregnant mare's urine, will inhibit bone loss when administered by themselves.

Accordingly, the present invention provides methods for inhibiting bone loss comprising administering to a patient in need of treatment an effective amount of d-equilenin, 17β-dihydroequilenin, or 17α-dihydroequilenin, or a pharmaceutically acceptable salt thereof. The inhibition of bone loss contemplated by the present methods includes both medical therapeutic and/or prophylactic treatment, as appropriate. Thus, a "patient in need of treatment" contemplates an individual who is suffering from bone loss as well as one who is at risk of future bone loss. Also provided are pharmaceutical compositions comprising d-equilenin, 17β-dihydroequilenin, or 17α-dihydroequilenin, together with a pharmaceutically acceptable carrier, diluent, or excipient.

The compounds used in the methods of the present invention are well known in the art, and are represented below as d-equilenin (I), 17β-dihydroequilenin (II), and 17α-dihydroequilenin (III).

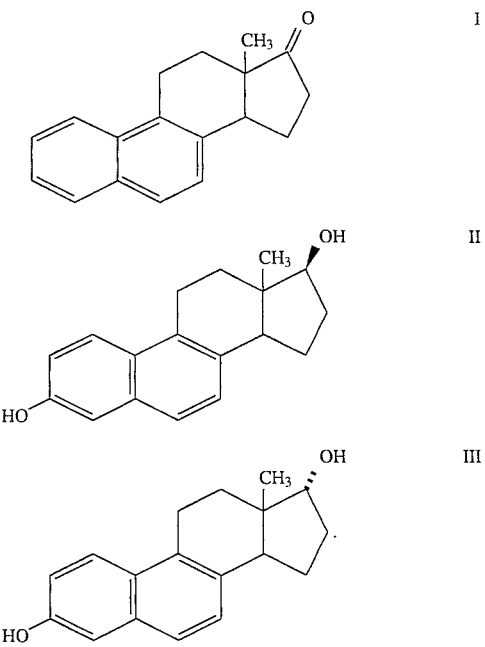

A compound of formula I, d-equilenin, is well known in the art and is commercially available (e.g., Sigma Chemical Company, St. Louis, Mo.), isolated from urine of pregnant mares see, e.g., Giraund, et al., *Cemot. Rend*, 195:981–983 (1932)], or prepared by any one of various known methods [see, e.g., *The Total Synthesis of Natural Products*, Vol. 2:642–663, ApSimon, Ed. (John Wiley & Sons, New York, 1973); Narashimhan, et al., *J, Chem. Soc. Perkin Trans. 1:* 1435–1439 (1984); and *J. Chem. Soc. Chem. Commun,:* 1544–1546 (1990)].

Similarly, 17α- and 17β-dihydroequilenin can be isolated from the urine of pregnant mares, or it can be prepared from d-equilenin via procedures well known to one of ordinary skill in the art. Typically, 17β-dihydroequilenin is prepared from d-equilenin via standard reduction procedures, essentially as described by David in *Acta Brev. Nederland*, 4:63 (1934) or Carol, et al., in *J. Biol. Chem.*, 185:267 (1950).

Once the 17β-dihydroequilenin is prepared, the 17α-dihydroequilenin is prepared via a standard inversion reaction [see, e.g., Ochsner, et al., *Steroids*, 42:555 (1983)].

Compounds of formulae I, II, and IV occur in nature as sulfate esters. These compounds can be used as such in the methods of the present invention or, preferably, are desulfated prior to administration for bone loss inhibition. Desulfating is carried out via standard procedures. In addition, pharmaceutically acceptable salts of compounds of formulae I, II, or III, as prepared via standard procedures, also may be used in the methods of the present invention.

TEST PROCEDURES

Inhibition of Bone Loss I

Six month old, female Sprague Dawley rats (weight range of 275 to 350 g; Harlan Sprague Dawley, Indianapolis, Ind.) are used in these studies. Ovariectomies (or a sham surgical procedure for controls) are performed by the vendor. The animals are shipped the day following surgery and housed in hanging wire cages. Room temperature is maintained at 22.2°±1.7° C. with a minimum relative humidity of 40%, and the room is maintained on a 12 hour light/dark cycle with onset at 0600 hrs. The animals have ad lib access to food (Teklad diet, TB 89222, 0.5% calcium 0.5% phosphorus; Madison, Wis.) and water, and are allowed one day to acclimate to these post-delivery conditions prior to experimental manipulation.

Preparations of formula I, II, or III are made in 20% β-cyclodextrin (CDX) with 20% CDX as the control vehicle. 17α-Ethynyl-estradiol (obtained from Sigma Chemical Co., St. Louis, Mo.) also dissolved in 20% CDX is used as an internal standard for these studies.

On the third day post-ovariectomy, dosing with test compounds is initiated. Oral gavages of 20% CDX, a compound of formula I, II, or III (0.01 to 10 mg/kg) or an internal standard are delivered daily for 35 consecutive days. On the evening following the final dose, the animals are fasted. The animals are anesthetized with a mixture of Ketaset® and Rompum® (67 and 6.7 mg/kg, respectively) the next morning, and a 3-mL sample of blood is obtained by cardiac puncture. The animals are then asphyxiated with carbon dioxide, and body weight and uterine weight are recorded. The left femora and tibiae are removed from each animal for subsequent x-ray evaluation.

The distal end of the femur is x-rayed using a Norland NXR-1200 x-ray machine with a voltage of 47 kV and contrast at 4.5. Digitized x-ray images are transferred directly to a Macintosh computer station, and image analysis of the x-ray scan is conducted using the Ultimage software program. Quantitation is achieved by measuring the total number of pixels in a standard region of interest proximal to the growth plate, over an optimal gray scale range generally from zero to 60.

Alternatively, a 960 pQCT (Norland/Stratec, Ft. Atkinson, Wis.) is used to analyze the volumetric mineral density (mg/cm$^3$) and mineral content (mg) of proximal tibiae, using Dichte software version 5.1 and a voxel size of 0.149× 0.149×1.0 mm. Using hydroxyapatite phantoms and different regions of a COMAC European Forearm phantom, an accuracy of 9% (TMD, mg/cm$^3$ hydroxyapatite) was derived for this instrument, with a precision of 1%. Data with d-equilenin are described in Table 1 for 6–8 rats in each group. A "★" designation denotes statistical significance from Ovx, as compared by one way analysis of variance ($p<0.023$, Fisher PLSD).

TABLE 1

| Proximal Tibiae of D-Equilenin Treated Rats | | |
|---|---|---|
| Group (n = 6) | Volumetric Bone Mineral Density (mg/cm$^3$) | Bone Content (mg) |
| Sham | 636 ± 15* | 12.5 ± .38* |
| Ovx | 537 ± 11 | 10.0 ± .27 |
| 0.1 mg/kg/day | 562 ± 11 | 11.0 ± .25 |
| 1.0 mg/kg/day | 568 ± 13 | 10.7 ± .39 |
| 3 mg/kg/day | 615 ± 9* | 11.4 ± .46* |
| 10 mg/kg/day | 600 ± 9* | 11.1 ± .34* |
| Ethynyl Estradiol | 608 ± 11* | 12.0 ± .20* |

Compounds of formulae I, II, and III as described above are useful for inhibiting bone loss while improving the margin of safety for the patient compared to standard estrogen therapies.

Inhibition of Bone Loss II

Fracture rate as a consequence of bone loss is inversely correlated with bone mineral density. However, changes in bone density occur slowly, and are measured meaningfully only over many months or years. It is possible, however, to demonstrate that the formulae I, II and III compounds have positive effects on bone mineral density and bone loss by measuring various quickly responding biochemical parameters that reflect changes in skeletal metabolism. Typically, patients are treated for a period of from 8 weeks to 3 years. Blood and urine are collected before, during and at the conclusion of treatment. Estrogen administration and placebo serve as the positive and negative controls, respectively.

The patients are either healthy postmenopausal (surgical or natural) women, age 45–65 who would be considered candidates for estrogen replacement therapy for potential bone loss, or patients of the same age group or older who have shown clinical signs of bone loss (e.g., shortened stature).

Patients who have received any of the following medications at the beginning of the study are systematically excluded from the study; vitamin D, corticosteroids, hypolipidemics, thiazides, antigout agents, salicylates, phenothiazines, sulfonates, tetracyclines, neomycin, and antihelmintics. Patients who have received any estrogen, progestin, or androgen treatment more recently than three months prior to the beginning of the study; patents who have ever received calcitonin, fluoride, or bisphosphonate therapy; patients who have diabetes mellitus; patients who have a cancer history anytime within the previous five years; patients with any undiagnosed or abnormal genital bleeding; patients with active, or a history of, thromboembolic disorders; patients who have impaired liver or kidney function; patients who have abnormal thyroid function; patients who are poor medical or psychiatric risks; or patients who consume an excess of alcohol or abuse drugs.

Patients in the estrogen treatment group, when used, receive 0.625 mg/day and the test groups for compounds of formula I receive dosages from 0.1 mg to 50 mg, preferably 1 mg to 20 mg per day, all groups receiving oral capsule, tablet, or solution formulations.

The study is of double-blind design with both primary care physicians and patients ignorant of the treatment group to which the patient is assigned.

A baseline examination of each patient includes quantitative measurement of urinary calcium, creatinine, hydroxyproline, and pyridinoline crosslinks. Blood samples are measured for serum levels of osteocalcin, bone-specific alkaline phosphatase, and cholesterol levels. Baseline measurements also include examination of the uterus including uterine biopsy.

During subsequent visits to the investigating physician, measurements of the above parameters in response to treatment are repeated.

Subsequent longer term studies can incorporate the direct measurement of bone density by the use of dual photon x-ray absorptiometry (DXA or OCT), and the measurement of fracture rates associated with treatment regimen.

The term "an effective amount" is used in the present document to describe the dose of a compound of Formula I, an antiresorptive agent or an anabolic agent, and is defined as the dose which provides effective treatment or prevention to the patient.

The administration of compounds of formulae I, II, or III in order to practice the present methods of therapy is carried out by administering an effective amount of the chosen compound to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment. It will be observed that the compounds are active at very low concentrations, and hence at low dosage levels, thereby allowing effective inhibition of bone loss with slight probability of side effects or cross-reactions with other treatments or drugs. Accordingly, a typical daily dose of a compound of formula I is in the range of from about 0.02 mg to about 200 mg per day. More preferred ranges of daily dosage are from about 0.5 mg to about 50 mg. The compounds may be administered in a single daily dose, or the daily dose may be administered in portions at intervals through the day, as is preferred in the judgment of the physician.

The compounds of the methods of the present invention can be administered by a variety of routes including oral, rectal, transdermal, subcutaneous, intravenous, intramuscular, and intranasal, and such compounds are preferably formulated prior to administration. Therefore, another embodiment of the present invention is a pharmaceutical formulation comprising an effective amount of a compound of formula I, II, or III, or a pharmaceutically acceptable salt thereof, and a pharmaceutically acceptable carrier, diluent or excipient thereof.

The active ingredient in such formulations comprises from 1% to 99% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the composition of the present invention, the active ingredient(s) will usually be admixed with a carrier which may be in the form of a capsule, sachet, paper, or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients.

|  | Quantity (mg/capsule) |
| --- | --- |
| Compound of formula I, II, or III | 20 |
| Starch, dried | 400 |
| Magnesium stearate | 10 |
| Total | 430 mg |

Formulation 2

A tablet is prepared using the ingredients below:

|  | Quantity (mg/capsule) |
| --- | --- |
| Compound of formula I, II, or III | 40 |
| Cellulose, microcrystalline | 600 |
| Silicon dioxide, fumed | 10 |
| Stearate acid | 5 |
| Total | 655 mg |

The components are blended and compressed to form tablets each weighing 655 mg.

Formulation 3

| Compound of formula I, II, or III | 10 mg |
| --- | --- |
| Starch | 70 mg |
| Microcrystalline cellulose | 60 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl—pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 4

Capsules, each containing 80 mg of active ingredient, are made as follows:

| | |
|---|---:|
| Compound of formula I, II, or III | 80 mg |
| Starch | 58 mg |
| Microcrystalline cellulose | 58 mg |
| Magnesium stearate | 4 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 5

Suppositories, each containing 25 mg of active ingredient per dose, are made as follows:

| | |
|---|---:|
| Compound of formula I, II, or III | 25 mg |
| Saturated fatty acid glycerid | 2,000 mg |
| Total | 2,025 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 50 mg of active ingredient per 5 ml dose, are made as follows:

| | |
|---|---:|
| Compound of formula I, II, or III | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

| | |
|---|---:|
| Compound of formula I, II, or III | 10 mg |
| Isotonic saline | 1,000 ml |

The solution of the above ingredients generally is administered intravenously to a subject at a rate of 1 ml per minute.

We claim:

1. A method of inhibiting bone loss comprising administering to a patient in need of treatment an effective amount of a compound of formula I, II, or III

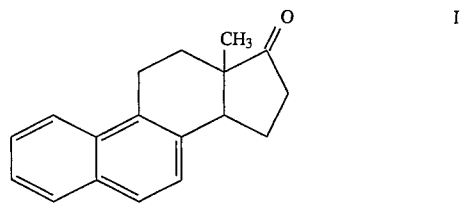

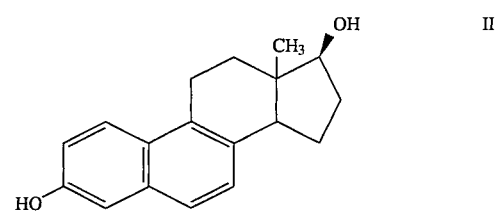

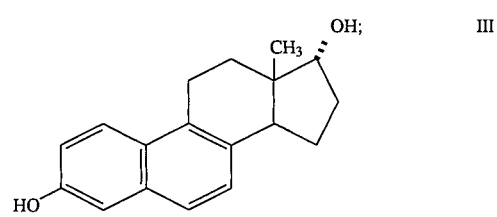

or a pharmaceutically acceptable salt thereof.

2. A method according to claim 1 wherein said compound is d-equilenin, or a pharmaceutically acceptable salt thereof.

3. A method according to claim 1 wherein said compound is 17β-dihydroequilenin, or a pharmaceutically acceptable salt thereof.

4. A method according to claim 1 wherein said compound is 17α-dihydroequilenin, or a pharmaceutically acceptable salt thereof.

5. A method according to claim 1 wherein said patient is a female.

6. A method according to claim 5 wherein said female is a postmenopausal woman.

7. The method of claim 1 wherein said compound is administered by itself.

* * * * *